US007901558B2

(12) United States Patent
Curcio et al.

(10) Patent No.: US 7,901,558 B2
(45) Date of Patent: Mar. 8, 2011

(54) INTEGRATED 2D GEL ELECTROPHORESIS METHOD AND SYSTEM

(75) Inventors: Mario Curcio, Sins (CH); Martin Kopp, Hagendorn (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1029 days.

(21) Appl. No.: 11/278,975

(22) Filed: Apr. 7, 2006

(65) Prior Publication Data

US 2006/0226010 A1  Oct. 12, 2006

(30) Foreign Application Priority Data

Apr. 11, 2005  (EP) ..................................... 05007912

(51) Int. Cl.
*G01N 27/26* (2006.01)
*G01N 27/447* (2006.01)

(52) U.S. Cl. ......... 204/456; 204/466; 204/548; 204/606; 204/616

(58) Field of Classification Search .................. 204/466, 204/456, 548, 606, 616; 205/775
See application file for complete search history.

(56) References Cited

U.S. PATENT DOCUMENTS

| 5,795,749 | A * | 8/1998 | Wong et al. ..................... 435/105 |
| 6,277,259 | B1 | 8/2001 | Guttman et al. |
| 6,554,991 | B1 | 4/2003 | Goodman et al. |
| 6,599,410 | B1 | 7/2003 | Steiner et al. |
| 6,602,975 | B2 * | 8/2003 | Hubbell et al. ................ 528/354 |
| 6,676,819 | B1 | 1/2004 | Liu et al. |
| 2002/0096431 | A1 * | 7/2002 | Sevigny et al. ................ 204/467 |
| 2002/0170825 | A1 * | 11/2002 | Lee et al. ........................ 204/455 |
| 2003/0127331 | A1 | 7/2003 | Leka |
| 2003/0207806 | A1 * | 11/2003 | Ensign et al. .................... 514/12 |
| 2004/0045829 | A1 | 3/2004 | Ingenhoven et al. |
| 2004/0050699 | A1 * | 3/2004 | Goncalves ..................... 204/450 |
| 2004/0112751 | A1 * | 6/2004 | Han et al. ....................... 204/605 |
| 2004/0144647 | A1 * | 7/2004 | Dorner et al. .................. 204/450 |
| 2005/0043490 | A1 * | 2/2005 | Klee et al. ...................... 525/285 |

FOREIGN PATENT DOCUMENTS

| EP | 0366897 A3 | 5/1990 |
| WO | 02/084273 A1 | 10/2002 |
| WO | WO 03/092846 A2 | 11/2003 |

OTHER PUBLICATIONS

Li et al., Integration of Isoelectric Focusing with Parallel Sodium Dodecyl Sulfate Gel Electrophoresis for Multidimensional Protein Separations in a Plastic Microfludic Network, Analytical Chemistry, vol. 76, Feb. 1, 2004, pp. 742-748.*

(Continued)

*Primary Examiner* — Alexa D Neckel
*Assistant Examiner* — Jennifer Dieterle
(74) *Attorney, Agent, or Firm* — Roche Diagnostics Operations, Inc.

(57) ABSTRACT

Described is a process for the separation of a sample mixture for analytical reason based on two-dimensional gel electrophoresis. The method is involving a first separation in a first gel strip on the basis of isoelectric points and a second separation in a second gel on the basis of molecular size. When starting the separation in the second dimension the buffer solution for transferring the compounds separated in the first dimension into the second dimension gel is containing sodium dodecyl-sulfate (SDS) and by applying an electric field the SDS migrates electrokinetically into the first gel strip, and the compounds are being complexed simultaneously with SDS.

12 Claims, 7 Drawing Sheets

OTHER PUBLICATIONS

Simpson, Proteins and Proteomics: A Laboratory Manual, CSHL Press, ISBN 0879695544, 9780879695545, published 2003, pp. 349-351.*

Sobotka et al., Advance in Clinical Chemistry, Academic Press, 1961, p. 214.*

Linse et al., Phase behavior of poly(ethylene oxide)-poly(propylene oxide) block copolymers in aqueous solution, The Journal of Physical Chemistry, vol. 97, No. 51, 1993, p. 13896-13902.*

Rill et al. (Peptide separations by slab gel electrophoresis in Pluronic F127 polymer liquid crystals, Electrophoresis 2004, 25, 1249-1254).*

Li, Y. et al., "Integration of Isoelectric Focusing with Parallel Sodium Dodecyl Sulfate Gel Electrophoresis for Multidimensional Protein Separations in a Plastic Microfludic Network," Anal. Chem. 2004, 76, 742-748.

O'Farrell, P. et al., "High Resolution Two-Dimensional Electrophoresis of Proteins," The Journal of Biological Chemistry, vol. 250, No. 10, May 25, 1975, 4007-4021.

Herbert, Ben et al., Reduction and alkylation of proteins in preparation of two-dimensional map analysis: Why, when, and how?, Electrophoresis, 2001, pp. 2046-2057, vol. 22.

O'Farrell, Patrick H., High Resolution Two-Dimensional Electrophoresis of Proteins, The Journal of Biological Chemistry, May 25, 1975, pp. 4007-4021, vol. 250, No. 10.

Sebastiano, Roberto et al., A new deuterated alkylating agent for quantitative proteomics, Rapid Communications in Mass Spectrometry, 2003, pp. 2380-2386, vol. 17.

Unlu, Mustafa et al., Difference gel electrophoresis: A single gel method for detecting changes in protein extracts, Electrophoresis, 1997, pp. 2071-2077, vol. 18.

* cited by examiner

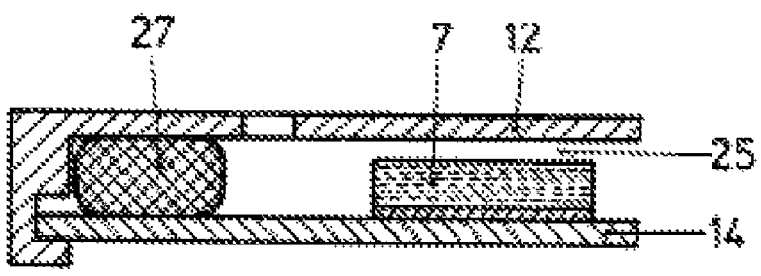
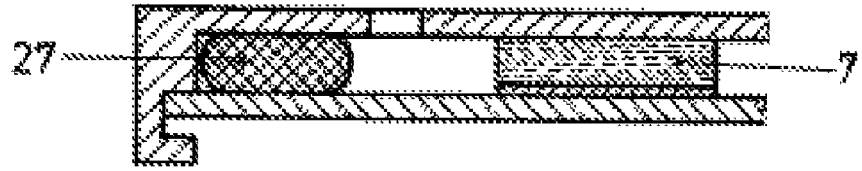
FIG. 5b
FIG. 5a

INTEGRATED 2D GEL ELECTROPHORESIS METHOD AND SYSTEM

RELATED APPLICATIONS

This application claims priority to EP 05007912.8 filed Apr. 11, 2005.

FIELD OF THE INVENTION

The present invention refers to a process for the separation of a sample mixture for analytical reason based on two-dimensional gel electrophoresis, in particular to an improved method in proteomics based on two-dimensional gel electrophoresis analysis and suggests a system or ways for integration and automation.

BACKGROUND OF THE INVENTION

Two-dimensional gel electrophoresis (2D-GE), since first published as a technique by O'Farrell (O'Farrell, P. H., J. Biol. Chem. 250:4007-21, 1975), has been for nearly 30 years the work horse in proteomics analysis, documented by thousands of application papers, and the object of numerous development and optimization attempts. Improvements occurred indeed and although alternative techniques, based on a different approach such as multidimensional chromatography directly coupled to mass spectrometry, are gaining popularity, 2D-GE is in fact still the most used technique and it might be still for several years if further improvements are achieved. Describing the details and advantages of 2D-GE in all its various forms is out of the scope of this invention as several reviews can be retrieved in the literature. It is however important to point out what the limitations of the general method still are and for this a general description of the process is only given.

Briefly the first dimension separation consists of isoelectric focusing (IEF) where proteins separate according to their isoelectric points in a pH gradient, typically immobilized (IPG), in a long and narrow supported gel assuming the form and taking the name of strip. The strips, commercially available, are normally supplied in a semi-dry state and they have to be rehydrated with the sample solution before analysis. This operation takes from a few hours to typically overnight and usually takes place under mineral oil to prevent drying and crystallization of urea present in the sample solution. IEF takes place also under mineral oil for the same reasons in the same or a different tray with the strip in contact with two electrodes at the sides, between which a high voltage is applied. After IEF the strip has to be equilibrated, which means that the proteins focused within the strip have to be first alkylated and then complexed with sodium dodecyl sulfate (SDS) in order to be later transferred to the second dimension gel and separated according to size. Reduction/alkylation can be achieved by different reagents and one has the option to perform this step during sample preparation before rehydration. It is actually recommended to do so (Herbert et al., Electrophoresis 22:2046-2057, 2001). However SDS equilibration can be performed only after IEF, so that the strip is literally washed for several minutes in the equilibration solution containing SDS. This is then placed on top and in contact with a prepolymerized SDS polyacrylamide gel and coupling is normally achieved by pouring a hot agarose solution over the strip. This is usually accomplished between two glass plates which are clamped together and then placed in a buffer containing cassette where voltage is applied across the gel. The gel might be formed with a porosity gradient in order to increase resolution in the second dimension. After this is complete, the gel is removed, fixed, stained and background staining dye removed before proceeding eventually with the subsequent steps, i.e. spot picking, digesting and mass spectrometry analysis.

All this is not only a time-consuming and laborious procedure, requiring trained personnel, but just because there is much manual work involved, reproducibility is still the major issue, as gels are mostly made to be compared. Although running conditions can be quite reproducible as these are controlled by proper set-up and power supplies, especially if fresh buffers are used all the time, problems with accuracy and consistency can arise from variations in the other numerous parameters to keep under control. For example, storage time (degradation) of precast gels prior to use, sample loading and rehydration, in terms of sample amount, losses, and homogeneity of the strip, strip handling with risk of damaging and contamination, equilibration between first and second dimension with risk of loosing sample and resolution, imprecise coupling to the gel, gel casting and polymerization, in terms of homogeneity, air sensitivity and risk to trap bubbles causing consequently also field inhomogeneities.

Ideally, what is desirable is that no further manual intervention is required after the sample has been loaded and that the overall process time is also reduced with the possibility to run several gels in parallel and increase not only the reproducibility but also the throughput while reducing the cost per gel. Automation and integration of the steps of this complex procedure is a challenge that others have already faced. Approaches making use of channels for separations instead of gels are not considered here as they are not directly comparable, neither are their performances, and because different parameters and limitations come into play.

An integrated, fully automated, system mimicking step by step the manual procedure, including also sample preparation and strip casting is described in U.S. Pat. No. 6,554,991 B1. The robotic machinery behind it, the complexity of the operation and the investment necessary go however far beyond a practical and widespread use of it, especially among the smaller research laboratories. US 2003/0127331 discloses a system where the strip once cast at the bottom of a vertical mold formed by two plates doesn't have to be moved after IEF. It is understood that the strip can be treated with the equilibration solution, apparently just from one side, and subsequently coupled to the second dimension gel by pouring the gel solution into the mold directly in contact with the strip or on top of an agarose layer. Doubts remain however concerning the efficiency and/or the time of the equilibration with the SDS having to diffuse inside the strip just from one side and whether the resolution obtained in the first dimension can be preserved. As no mention is made concerning the polymerization method, the long times associated with the classical method increase further the concern about loss of resolution. Also, the way the strip is formed and the sample is added is less reproducible and the fact that a sealing tab at the bottom of the mold has to be removed at the end is not practical. In EP 0366897 it is proposed that the strip is first separated from a prepolymerized gel by means of a non-conductive phase-change material, which is melted after IEF by increasing the temperature, removed and substituted with other gel medium. No reference is however made to the equilibration step and besides the concerns about the effect of the temperature for proteins and gel, remains the problem associated with closing and opening this time the top of the mold. Other barrier means between strip and gel are proposed in WO 02/084273 A1. The first embodiment reported therein making use of sliding solid barriers is certainly not the most advantageous as formed gels might be disrupted by this action. More interesting solutions make use of pneumatically assisted valves consisting of soft and expandable material or of semi-walls at the sides of the strip, which is physically bound as well as the gel on a flexible and peelable foil. This foil can change position relative to the opposite rigid surface, thus opening and closing the strip chamber. The gel solution is in this case introduced and polymerized after opening the strip chamber at the end of the first dimension. Equilibration solutions can access the strip through slits correspondingly positioned on the rigid part of the device. An automated system eventually based on this principle will be commercialized by Nextgen Sciences in the near future. This however reproduces also the same steps which are otherwise carried out manually, thus demanding a certain complexity due to valves and moving parts and adding cost for the instrument, also this less affordable. Other weak points of this system are represented by dead volumes for the sample, certain loss of resolution due to the equilibration between first and second dimension and the long waiting time for gel polymerization. Within the U.S. Pat. No. 6,277,259 an automated two dimensional gel electrophoresis of proteins is described, using thin linear gels. The protein sample is dissolved and complexed and processed in a first dimension separation followed by migration into a second dimension separation, labelled by a dye e.g. a fluorescent labelling to enable detecting the proteinaceous sample during second dimension separation. Within the WO 03/092846 a two dimensional analysis in a micro fluidic format using microchannels is described for performing two dimensional separations.

A cheaper, simpler, quicker and equally integrated solution in the form of a disposable, specially designed for minigel format is offered by Roche Diagnostics as described in a previous not yet published EP application (EP 04 015 469.2 attached to this application).

SUMMARY OF THE INVENTION

It is consequently object of the present invention to propose an improved method in proteomics based on two-dimensional gel electrophoresis analysis and a respective system or respective ways enabling at least partial automation and integration of the above described steps and helping to overcome the problems and disadvantages described above related to the process steps known in the state of the art, which are by the majority still manually executed.

Accordingly, the present invention provides a process for the separation of a sample mixture for analytical reason based on two-dimensional gel electrophoresis, the method involving a first separation in a first gel strip on the basis of isoelectric points and a second separation in a second gel on the basis of molecular size characterized in that when starting the separation in the second dimension, a buffer solution, for transferring the compounds separated in the first dimension into the second dimension gel, is containing sodium-dodecyl-sulfate (SDS) and that by applying an electric field the SDS migrates electrokinetically into the first gel strip, and the compounds are being complexed simultaneously with SDS. The present invention further provides an analytical system for the separation of a sample mixture for analytical reason based on two-dimensional gel electrophoresis, wherein a first gel strip is used consisting of a hydrophilic material.

The present invention refers to a new generation of the previous disposable and automation concept, achieving increased simplicity, reducing further the costs and offering higher resolution and reproducibility. In order to achieve this, a modification of the general method, as described above, was necessary. The description of the invention is thereby the description of a method where possible conditions and embodiments are suggested at each step in order to obtain an integrated and automated system.

BRIEF DESCRIPTION OF THE DRAWINGS

FIG. 5 shows schematically another possible solution to the problem described in Step 4 below, where by way of a cross-sectional view part of the analytical disposable is shown in the area of the first gel strip 7.

DETAILED DESCRIPTION OF THE INVENTION

For simplification reasons and for the better understanding of the present invention the various method or process steps for the two-dimensional gel electrophoresis analysis are described in operational sequence. Below is a brief list of the steps involved during the execution of the developed method followed by a discussion for each of them:

1. Perform reduction/alkylation prior to IEF (isoelectric focusing)
2. Load sample.
3. Run IEF in any of the following proposed ways.
4. Increase spacing between strip and opposite surface of the gel mold.
5. Bring gel solution for 2nd dimension separation while achieving coupling at the same time and polymerize.
6. Bring SDS to the focused proteins electrokinetically.
7. Replace running buffer and run 2nd dimension.
8. Open gel mold to remove gel.
9. Proceed with fixing and staining.

Within the following description of the various steps also reference is made to the attached drawings, in which examples of possible embodiments and parts of the inventively developed system or device respectively are shown.

Step 1

Reduction/alkylation is performed just before sample loading as the last step of the sample preparation according to Sebastiano et al., Rapid Commun. Mass Spectrom. 17:2380-2386, 2003. Same reducing and alkylating reagents, i.e. tributylphosphine (TBP) and vinyl pirydine (VP) are preferably used, although with a slight modification of the method. It has been found that it is not necessary to buffer the sample solution for the alkylation reaction to occur, thus avoiding a useless increase of the salt concentration that would result in high current and longer IEF times unless desalting is carried out.

Moreover, it is considered more efficient to add TPB and VP in two consecutive steps rather than simultaneously since the two reagents can react with each other. In this way, shorter reaction times, e.g. overall 30 min, are also needed. As an example, a typical solution used to solubilize the protein sample, with variations of course allowed, consists of:

| | |
|---|---|
| Thiourea | 2 M |
| Urea | 7 M |
| CHAPS | 2% (w/v) |
| Bio-Lyte ® 3/10 Ampholytes | 0.5% (v/v) |
| Bromophenol Blue | 0.002% (w/v) |
| 1,2-propandiol | 20% |

To this, TBP is added e.g. first in concentration of 5 mM for about 10 min, followed by addition of VP 20 mM final concentration for about 20 min and again TBP in sufficient molar amount to quench the excess of the previous reagent, rather than a different reducing agent such as dithioerythryol (DTE).

The function of the 1,2 propandiol, which is a favorite additive among others possible as, e.g., glycerol, PEG, diethylenglycole, is to minimize EOF during IEF while maintaining the viscosity of the sample solution low, which is important for the sample loading step as will be seen below.

Step 2

Figure 1:
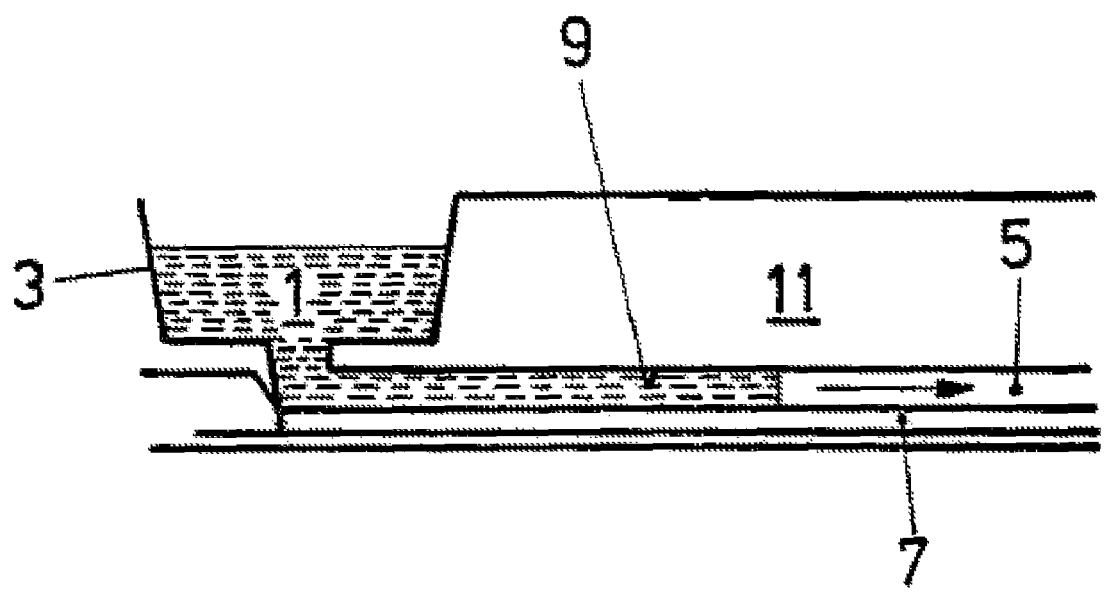
FIG. 1 shows in longitudinal section part of the first gel strip arranged within a 2D gel electrophoresis device or disposable respectively.

The sample, e.g. in the solution above, is inserted such as e.g. pipetted into a small sample well from which the sample can get in contact with the strip and the internal surface of the disposable body directly facing the strip and be guided as proposed according to the present invention by capillary hydrophilic forces between such surface and the semi-dry strip filling entirely the volume so defined and shown in FIG. 1. FIG. 1 shows in longitudinal section part of the first gel strip arranged within a 2D gel electrophoresis device or disposable respectively. The sample 1 as described above is inserted in a sample well 3 and is guided along a capillary opening 5 along the hydrophilic gel strip 7 in the direction of the shown arrow. Preferably, but not necessarily the area in correspondence of the strip is hydrophilic, while at least part of the rest of the surface 9 of the disposable body 11 is hydrophobic or otherwise non gel sticking. Contribution to sample guiding might be given simply also by two drawn parallel lines on the disposable body reproducing the size of the strip underneath. Gel sticking might be desirable on the same cover plane where the strip is attached, which can then be all hydrophilic or have gel bond properties. If this is a e.g. foil, the advantage is that at the end it can be peeled together with the gel, making handling easier and minimizing the risk of breakage. Pressure or vacuum may be employed to assist the loading but can in general be avoided. In this controlled way, a volume of sample corresponding exactly to the amount needed to rehydrate the strip can be introduced minimizing waste. Sample loading, rehydration and IEF are preferably carried out with the disposable in horizontal position.

Step 3

Figure 2:
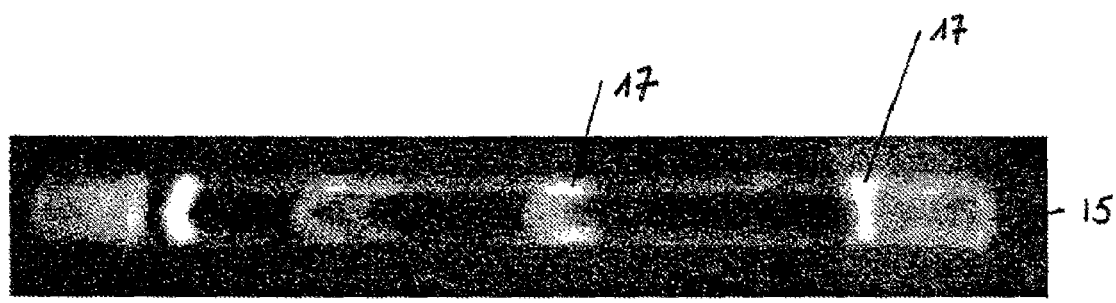
FIG. 2 shows a pluronic strip 15 with the separately located protein components 17 after the isoelectric focusing step.
Figure 3:
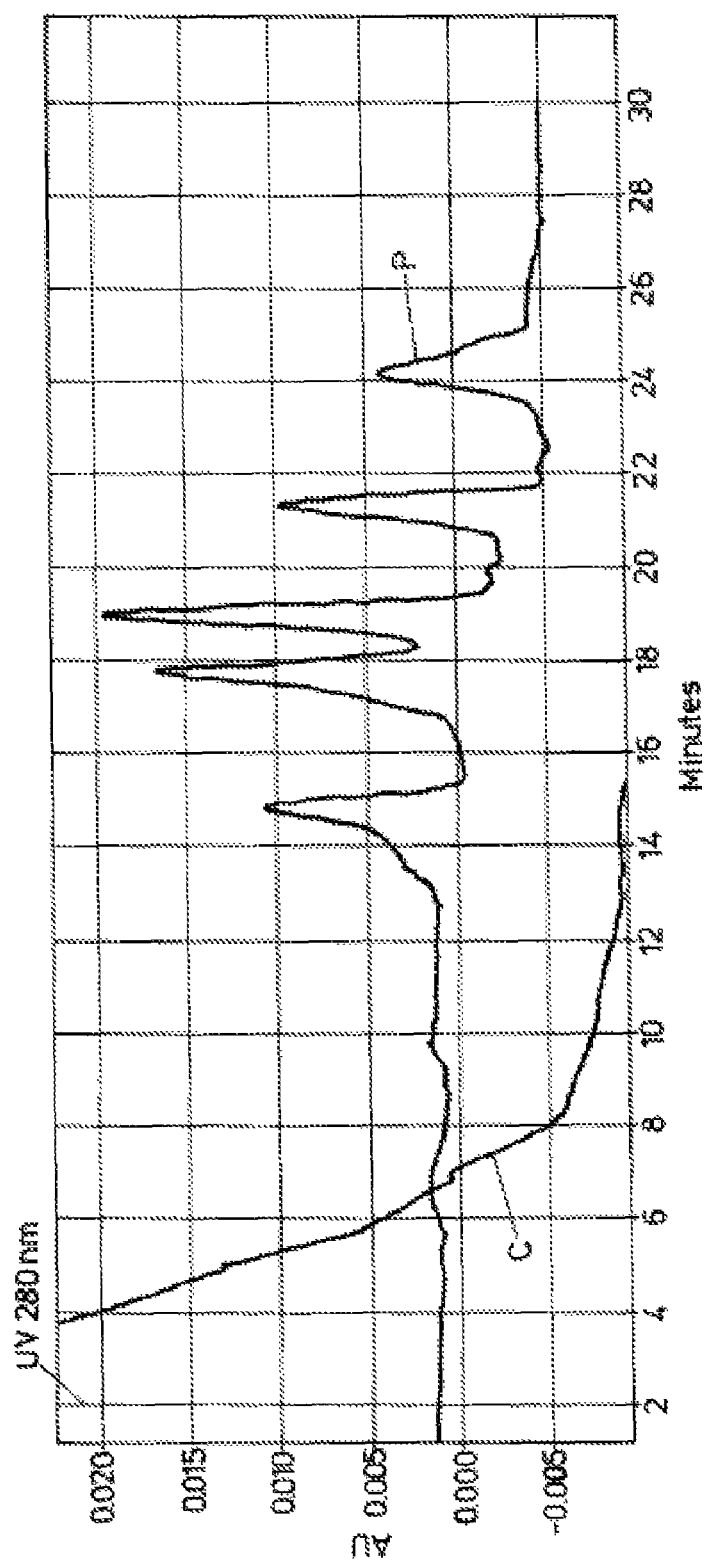
FIG. 3 shows in diagram form the separation of the same sample by capillary IEF in a pluronic filled capillary.

To be noticed is the fact that the strip 7 has not to be closed at its sides by any valves. Evaporation is minimized because the gel mold is nearly closed at all sides and because temperature is preferably kept cool during IEF being the disposable positioned e.g. on a cooling plate. Commercially available strips can be used, which would be already integrated in the closed compact disposable or otherwise separately supplied attached to the cover, which would close the main disposable body. Strips may also be polymerized in situ using the same system of hydrophilic guiding, this time on both surfaces, or otherwise a hydrophilic neutral porous material, e.g. a membrane with a strip shape. In this case, however, instead of passive rehydration we would have an active sample loading. Disclosed here is also a new IEF medium, which might be premixed with the sample solution, guided as above to assume a strip shape and capable of gelling when increasing the temperature slightly above room temperature. A medium with this characteristic is a block copolymer of ethylene oxide and propylene oxide belonging to the class of commercially available products known as Pluronics from BASF. A possibly suitable one is e.g. Pluronic F127 at a concentration of about 20% or above when mixed with a sample solution such as that described above. This product besides other commercial applications has already been used as efficient sieving medium in capillary electrophoresis of oligonucleotides and sometimes of peptides but was never used for IEF of proteins. A normal characteristic of this copolymer when dissolved in water solution at a critical concentration is to be liquid at low temperature, typically <5° C. and become a sort of liquid crystalline gel at room temperature. The presence of urea, thiourea, ampholytes and detergents in the sample solution shifts the gelling point above 30-35° C., thus making the liquid, although viscous, easy to handle and guide at room temperature. Both in capillary electrophoresis and in the shape of a strip it was possible to obtain nicely focused proteins as shown in FIGS. 2 and 3. FIG. 2 shows a pluronic strip 15 with the separately located protein components 17 after the isoelectric focusing step. FIG. 3 shows in diagram form the separation of the same sample by capillary IEF in a pluronic filled capillary. Here, the line C represents the current drop during IEF while the line P shows the IEF peaks following mobilization. The advantage in capillary electrophoresis is that uncoated capillaries can be used due to the dynamic coating properties of the polymer itself.

Step 4

Figures 4A, 4B:
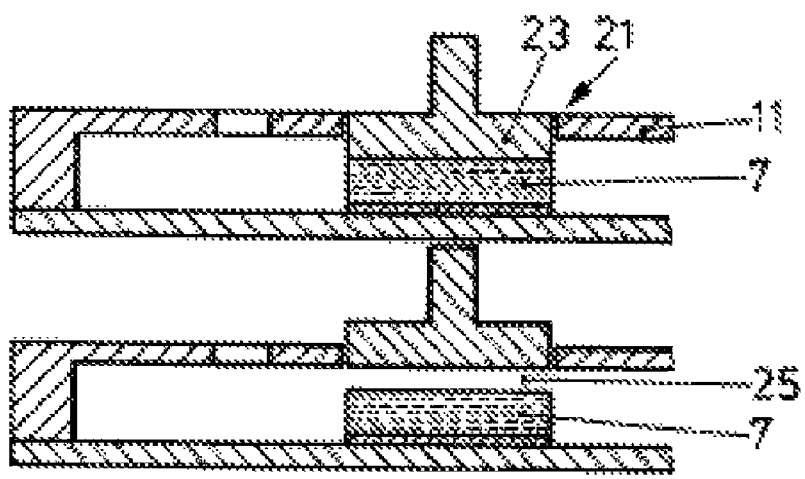
FIG. 4 shows schematically a possible solution to the problem described in Step 4 below, where by way of a cross-sectional view part of the analytical disposable is shown in the area of the first gel strip 7.
Figures 6A, 6B:
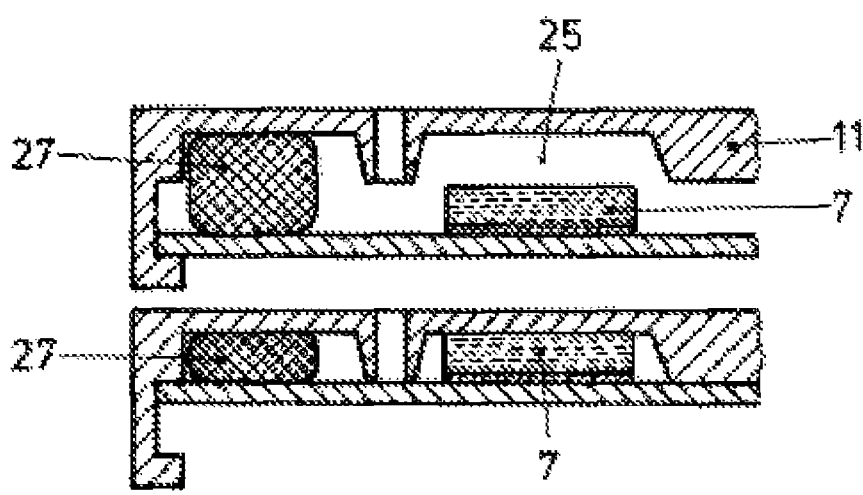
FIG. 6 shows schematically yet another possible solution to the problem described in Step 4 below, where by way of a cross-sectional view part of the analytical disposable is shown in the area of the first gel strip 7.

A problem experienced, at least with commercial strips, is represented by an irreproducible second dimension when the strip and the second dimension gel, polymerized directly in contact with the strip, have the same thickness. On one hand a spacing of the mold corresponding to the thickness of the rehydrated strip is necessary in order to introduce the right amount of sample, rely on a good capillary force and perform a good first dimension analysis. On the other hand a small space above the strip is required to achieve proper coupling with the gel and perform a good second dimension analysis. To solve this problem, three possible solutions are shown schematically in FIGS. 4 to 6, where by way of a cross-sectional view part of the analytical disposable is shown in the area of the first gel strip 7. One way is to have constant thickness for the gel mold and change thickness only in correspondence of the strip. For example, one can have a slit 21 in the disposable body 11 where a fitting bar 23 with a hydrophilic bottom 24 is automatically lowered and raised accordingly with two allowed positions as shown in FIGS. 4a and b. FIG. 4b shows the raised fitting bar 23 to shape a gap 25 above the strip 7. But other variants are possible, where e.g. the strip to move is attached either on a rigid or elastic component. Another way is to change the spacing of the entire gel mold between two allowed positions. For this purpose an elastic compressible frame 27—"O"-ring-like—can be inserted between two mold planes 12 and 14, as shown in FIGS. 5a and 5b and for these different geometries could be drawn. Eventually the two planes 12 and 14 can be brought to touch each other when the frame is squeezed as shown in FIG. 5a, while a cavity or a gap 25 is shaped between the upper mold plane 12 and the gel strip 7 when the compressible frame is expanded, as shown in FIG. 5b. A suitable cavity 25 with the same height of the strip 7 can be left in correspondence of the strip such as schematically drawn in FIG. 6. Again, FIG. 6*a* shows the compressible frame squeezed, while FIG. 6*b* shows the compressible frame in expanded condition. The mechanism of sample loading is preferably still the same but the air volume around the strip would be reduced.

Step 5

For more controllable gel casting this step is preferably carried out vertically, which means that the instrument will operate a 90° rotation of the disposable. The introduction of the gel solution can occur through proper tubing fitting or needle either from the bottom to the top or from the top to the bottom and the strip may find itself located at any of the four sides relative to the vertical mold. In this way the gel solution will fill completely the mold, at least partially contacting, covering and/or enclosing the strip and it is preferable in order to maintain the resolution of the first dimension and diffusion of acrylamide inside the strip, with possible crosslinking to the sample, that polymerization occurs rapidly. For this reason the traditional method, making use of ammonium persulfate (APS) and N,N,N',N'-tetramethylethylene-diamine (TEMED) as initiator and catalyst respectively of radical polymerization, is not preferred because these reagents have to be added and mixed at the last moment as they start immediately polymerization already during casting and because the reaction proceeds slowly taking normally more than one hour to be completed. Ideally, the gel solution contains already the reagents for polymerization and is stable under storage conditions; important is also that once the reaction is triggered, e.g. by external energy source, this proceeds fast, while maintaining the characteristics of the traditional sieving gel. This can be achieved for instance by UV-initiated polymerization choosing an intiator that is stable in the acrylamide gel solution until exposed to a light source whose wavelength range comprises its absorbance spectrum. UV transparent materials should be thereby used for the disposable. As these compounds are generally not polar, hence poorly soluble in aqueous solution, a modification of the gel solution is necessary. For example up to 10% diethylenglycole without compromising the performance of the gel can be used. A suitable initiator is for example 2,2'-dimethoxy-2-phenyl-acetophenone (DMPA) at concentration of 0.05% or below. By this, exposure of the gel mold to UVA light of sufficient power results in complete polymerization in less than 5 min.

Although photopolymerization itself is not new, it was never applied to our knowledge to two-dimensional gel based proteomics.

Steps 6 and 7

Figure 7:
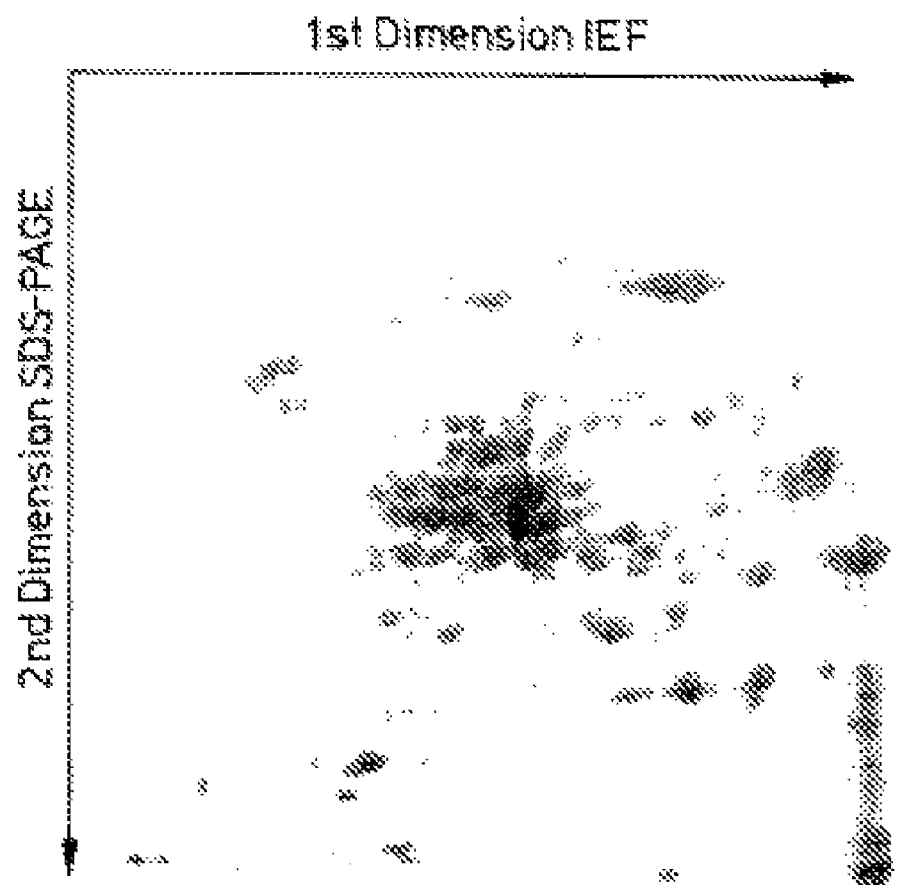
FIG. 7 shows the result of the two-D separation of an *E. coli* lysate, where a total sample amount of 150 µg was loaded on an IEF strip of 7 cm, pH range 4-7, and the second dimension separation was executed according to the present method based on SDS electrokinetic equilibration.

At this point the strip is coupled to the gel with the proteins focused in bands within the strip at their isoelectric points. This means however that carrying a zero net charge they won't be able to be transferred to the gel for the second dimension analysis. They have indeed been previously alkylated but are not yet complexed with Sodium-dodecyl-sulfate (SDS), which gives them a net negative charge and binds to them with a constant ratio allowing them to be separated now according to size through the sieving matrix of the gel. One way to bring SDS to the proteins is electrokinecally from the cathodic buffer reservoir. A concentration of SDS higher than that present in the running buffer is however necessary, e.g. 2% versus 0.1 or 0%. This has two implications: first the buffer at the cathode needs to be replaced or diluted after electrokinetic equilibration, second the distance of the strip from the buffer should preferably be small (e.g. <5 mm) in order to minimize the zone at high SDS concentration entering the gel. The resulting effect is however superior to the standard procedure. As the SDS migrates into the gel and encounters the protein bands, these start to mobilize from the tail while the head is still steady. The result is a stacking effect with the bands gradually compacting at the opposite side of the strip before beginning their migration and separation inside the gel, which in turn means a gain in resolution. In that respect FIG. 7 shows the result of the two-D separation of an *E. Coli* lysate, where a total sample amount of 150 μg was loaded on an IEF strip of 7 cm, pH range 4-7, and the second dimension separation was executed according to the present method based on SDS electrokinetic equilibration. The achieved resolution, shown in FIG. 7, appears clear to a person skilled in the field and was confirmed by mass spectrometry analysis, which proved also the absence of artifacts. Once proteins have complexed with SDS, the interaction is sufficiently strong so that no SDS needs actually to be present in the gel solution from the beginning. By this way we also make sure that no SDS diffuses into the strip from the gel solution causing partial complexation of the proteins and potentially disrupting the stacking effect described. SDS electrokinetic equilibration with the first buffer is preferably carried out at lower electric fields compared to the separating conditions. Applied is e.g. an electric field in the range of approximately 5 to 6 v/cm or lower. This step takes approximately 5-10 min, the time necessary for the SDS to pass through the strip, after which the run is paused e.g. for the time necessary to replace the buffer, the buffer at the cathode replaced or diluted, if starting from a smaller volume, and the run restarted at much higher electric fields for fast separation, while the heat is dissipated through efficient cooling. The strength of the higher electric field is dependent on the system and is preferably higher than e.g. approximately 20 volt per centimeter. If a higher electric field is applied, a higher cooling capacity of the system has to be applied. Preferably, the gel mold is closed from all sides between the two planes, e.g. by means of a squeezable frame as mentioned above in respect to FIGS. 5 and 6. The buffers contact the gel at two opposite edges of the mold and on the same plane, through two parallel slits, one of which positioned between the strip and one edge, and as close as possible to the strip for the reasons above. The slits are also preferably closed to prevent more efficiently evaporation and drying of the strip and to avoid gel solution leaking during casting in the vertical position. The slits might be created for example only when and where needed by cutting, with a blade function integrated in the instrument, thinner linings, that represent physical integral parts of the disposable body, e.g. made by injection molding. The slits could be otherwise sealed by a porous membrane, e.g. polyethylene, PES (polyethersulfone), polypropylene, or PET, with the right thickness and porosity and which withstand the extrusion pressure of the gel during casting but are then wetted by the buffer containing SDS thus establishing electrical contact with the gel. The use of tapes or adhesive tabs is preferably avoided from an automation point of view.

The way of bringing SDS electrokinetically to mobilize focused proteins is not new. There is one previous published work (Li et al., Anal. Chem. 76:742-48, 2004) in which however a different system is described with proteins focused first in a microfluidic channel and where SDS elctrokinetically introduced is necessary to inject separate zones into side channels. Here instead the first application to two-dimensional gel electrophoresis is reported and for the first time this stacking effect between strip and gel is described.

Steps 8 and 9

From sample loading to this point all steps could be automated. Once the second dimension run is completed, the user can remove manually the disposable from the instrument and take the gel off. Preferably, for easier handling, the gel remains attached to one of the surfaces of the mold, either the disposable body or the covering plane, which can consist either of a rigid plate, e.g. glass or polymer, or a polymeric more flexible foil. The surface where the gel sticks has to be consequently chemically accessible by polymerization process while the other has to be chemically inert towards the radical polymerization. The supported gel can be then processed according to the traditional procedure for fixing and staining.

CONCLUSIONS

A method is here disclosed for two-dimensional gel electrophoresis, which offers the following advantages over the prior art:

Increased resolution in the second dimension as a consequence of the stacking effect by SDS electrokinetic equilibration.

Prior alkylation and SDS elektrokinetic equilibration together eliminate the need of treating the strip with equilibration solutions between first and second dimension. This means avoiding handling or moving the strip or closing the strip with valves, avoiding extra buffers, avoiding the use of coupling agarose or other stacking gel, reducing the complexity of operation, either manual or automatic, saving time, which means also minimized band broadening by diffusion, hence increased resolution also for the first separation. Finally, eventual washing out of proteins that can occur when using equilibration solutions is no longer an issue. Last but not least increased reproducibility can be assured.

The use of a gel formulation, which can be quickly polymerized and is stable until an external light source is not applied, avoids problems associated with gel preparation, avoids the need of prepolymerizing the gel before IEF and separate it from the strip by means of barriers, avoids otherwise long waiting times with consequently loss of resolution within the strip.

Optional hydrophilic patterning or track guiding in correspondence of the strip makes sample loading and rehydration easy and more reproducible avoiding again the need for valves, or immiscible liquid insulators, such as sticky mineral oil, which needs to be washed out afterwards.

Finally makes it possible to form non IPG strips in situ, for which a new gel medium is proposed. The latter has the advantage to change phase from liquid to solid by increasing the temperature without need for polymerization, can be premixed homogenously with sample, shaped in the form of a strip as a liquid and transformed to gel before IEF or at the moment of coupling to second dimension.

Ways of modifying the internal spacing of the gel or a part of the gel space allow efficient coupling and transfer of the focused proteins from the first dimension to the second dimension.

The steps of the method can be integrated by proper designing of a device and an instrument, which assume the form of a disposable and low-complexity, low-cost, affordable, processing apparatus respectively.

Shorter overall analysis time and higher throughput are achieved.

Even if all the various new aspects and advantages have been described step by step above in an overall method or process respectively for the execution of a two-dimensional gel electrophoresis analysis, some of the inventively new aspects of the individual process steps can be taken independently into consideration, which means could be combined with process steps as known out of the state of the art. In principal the various independent aspects, which are new and inventive over the prior art could be considered as individual inventions, which not necessarily have to be combined with all the other new and inventive aspects as disclosed above.

What is claimed is:

1. A two-dimension method for separating compounds present in a sample mixture, the method comprising in the following order:
    (a) separating the compounds in a first-dimension gel strip on the basis of isoelectric points,
        at least partially contacting the first-dimension gel strip with a gel solution and performing a polymerization to obtain a second-dimension gel in contact with the first-dimension gel strip,
    (b) contacting the separated compounds in the first-dimension gel strip with a first buffer solution comprising sodium dodecyl sulfate (SDS),
    (c) applying an electric field to electrokinetically migrate the SDS into and through the first-dimension gel strip in a flow direction from a backside to a frontside of the first-dimension gel strip toward the second-dimension gel, wherein the separated compounds complex with the migrating SDS to form SDS-complexed compounds and are at least partially compacted at the front side of the first-dimension gel strip before migration into the second-dimension gel, and
    (d) separating the SDS-complexed compounds in the second-dimension gel on the basis of molecular size, wherein the SDS in the first buffer solution is present at a concentration higher than in a running buffer used in the second dimension.

2. The method of claim 1 wherein 1,2-propandiol is added to the sample mixture prior to separating the compounds in the first-dimension gel strip to reduce the electro-osmotic flow during the first dimension while maintaining low sample viscosity.

3. The method of claim 1 further comprising reducing and alkylating the compounds before the compounds are separated in the first-dimension gel strip.

4. The method of claim 3 wherein the reduction and alkylation step comprises contacting the compounds with tributylphosphine (TBP) and then vinyl pyridine (VP) without buffering the sample mixture.

5. The method of claim 3 wherein the first-dimension gel strip comprises a hydrophilic gel material and the sample mixture is placed in contact with the first-dimension gel strip after the reducing and alkylating step, wherein the sample mixture is guided or spread over the first-dimension gel strip by capillary hydrophilic forces, without the use of physical barriers or insulating liquids.

6. The method of claim 5 wherein the first-dimension gel strip comprises a block copolymer of ethylene oxide and propylene oxide, said block polymer formed from a copolymer solution.

7. The method of claim 6 wherein the copolymer solution comprises the sample mixture.

8. The method of claim 1 wherein the first buffer solution comprises SDS in a concentration of about 1% to about 3%.

9. The method of claim 8 wherein the SDS complexed compounds are subjected to an equal or higher electric field relative to the electric field applied when starting the migration of the complexed components into the second-dimension gel.

10. The method of claim 1 wherein the second-dimension gel is placed in contact with the first-dimension gel strip by polymerization of a preformulated gel composition to form the second-dimension gel and wherein the preformulated gel composition comprises an acrylamide gel solution and a UV initiator.

11. The method of claim 10 wherein neither the preformulated gel composition nor the second-dimension gel formed therefrom contains SDS.

12. The method of claim 11 wherein the preformulated gel composition further comprises diethylenglycol at a concentration selected from the range of about 5% to about 20% and 2,2'-dimethyloxy-2-phenyl-acetophenon (DMPAP) at a concentration of about 0.05% to about 0.2%.

* * * * *